United States Patent [19]

Seredenin et al.

[11] Patent Number: 5,439,930
[45] Date of Patent: Aug. 8, 1995

[54] BIOLOGICALLY ACTIVE N-ACYLPROLYDIPEPTIDES HAVING ANTIAMNESTIC, ANTIHYPOXIC AND ANOREXIGENIC EFFECTS

[75] Inventors: Sergei B. Seredenin; Tatiana A. Voronina; Tatiana A. Gudasheva; Rita U. Ostrovskaya; Grigori G. Rozantsev; Alexander P. Skoldinov; Sergei S. Trophimov, all of Moscow, Russian Federation; James A. Halikas, North Oaks, Minn.; Taisija L. Garibova, Moscow, Russian Federation

[73] Assignee: Russian-American Institute for New Drug Development, Bloomington, Minn.

[21] Appl. No.: 960,905

[22] Filed: Oct. 14, 1992

Related U.S. Application Data

[63] Continuation-in-part of Ser. No. 868,000, Apr. 14, 1992, abandoned.

[51] Int. Cl.$^6$ .................... A61K 31/40; C07D 207/12
[52] U.S. Cl. .................................. 514/423; 548/533; 548/537
[58] Field of Search ................ 548/533, 537; 514/423

[56] References Cited

U.S. PATENT DOCUMENTS

4,093,713 6/1978 Sestanj et al. ................ 424/177
4,743,616 5/1988 Tanaka et al. ................ 514/423

OTHER PUBLICATIONS

Journal of the Chemical Society, Perkin Transactions 1, No. 11, (Nov. 1990) pp. 3103–3108; B. C. Challis et al. "Synthesis and Characterisation of Some New N-Nitrosodipeptides".

Biopolymers, vol. 28, No. 1, (Jan. 1989) pp. 109–122, A. Aubry and M. Marraud, "Pseudopeptides and beta Folding: X-Ray Structures Compared with Structures in Solution".

Biopolymers, vol. 32, No. 3, (Mar. 1992) G. B. Liang et al., pp. 293–301, "Variations in the Turn-Forming Characteristics of N-Acyl Proline Units".

European Biophysical Journal, vol. 14, No. 1, (1986) pp. 43–51, M. McHarfi et al., "Backbone Side-Chain Interactions in Peptides".

Inorganic Chemistry, vol. 27, No. 22, (Nov. 2, 1988) pp. 4046–4052, Y. N. Belokon, "Copper(II) Ion Promoted Direct Hydrolysis of 2-Cyanopyridine to Picolinic Acid, Intramolecular Catalysis by the Coordinated N-beta-Hydroxyethyl Group".

Peptides 1990, Proceedings of the 21. Peptide Symposium, Sep. 2–8, (1990), E. Giralt and D. Andreu, 1991 ESCOM Publishers, Leiden, NL, pp. 462–464, G. Pietrzynski et al., "Conformational Propensities of Moel Peptides with Alpha, Beta-Dehydroamino Acids".

Journal of the Chemical Society, Perkin Transaction 1, (1981) pp. 1639–1646, J. S. Davies and R. J. Thomas, "Studies on the Diastereoisomeric and Conformational Aspects of Benzoyl Dipeptide Esters, as a Means of Assessing Racemisation using Neuclear Magnetic Resonance Spectroscopy".

(List continued on next page.)

Primary Examiner—Joseph Paul Brust
Attorney, Agent, or Firm—Merchant, Gould, Smith, Edell, Welter & Schmidt

[57] ABSTRACT

A novel class of substances of N-acyl-prolyldipeptides, which possess psychotropic activity and particularly facilitate learning and memory are described. The N-acyl-prolyldipeptides of the invention have the formula:

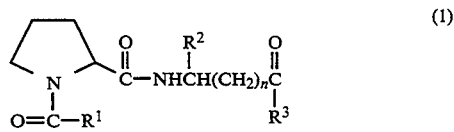

(1)

wherein $R^1 = (C_4-C_5)$ alkyl, cycloalkyl, aralkyl, or aryl; $R^2 = H_1$ ($C_1-C_4$) alkyl, carbamidoalkyl, or carbalkoxyalkyl; $R^3 = NH_2$, NH(alkyl), N(alkyl)$_2$, OH, or alkoxy; and $n = 0-3$, preferably 0–2.

25 Claims, No Drawings

OTHER PUBLICATIONS

Chemical Abstracts, vol. 111, No. 19, (Nov. 6, 1989), Columbus, Ohio, U.S.; abstract No. 16676, T. A. Gudasheva et al., "Topological Proline-based Analogs of Piracetam and their Nootropic Activity".

L. Amaducci et al., *Pharmacopsychiatry*, 23, 171–175 (1990).

A. Aubry et al., *Chem. Abs.*, 87, 614, Abstract No. 87:168404e (1977).

G. Boussard et al., *Chem. Abs.*, 81, 458, Abstract No. 81:136515b (1974).

G. Boussard et al., *Chem. Abs.*, 91, Abstract No. 91:141207p (1979).

T. A. Gudasheva et al., *Chem. Pharmac. J.*, 1985, N 11, pp. 1322–1329.

T. A. Gudasheva et al., *Chem. Pharmac. J.*, 1988, N 3, pp. 271–275.

G. B. Liang et al., *Chem. Abs.*, 116, Abstract No. 116:214897k (1992).

V. Y. Podlipskii et al., *Chem. Abs.*, 112, 780, Abstract No. 112:158881d (1990).

V. Y. Podlipskii et al., *Chem. Abs.*, 112, 786, Abstract No. 112:158955f (1990).

R. C. Thompson et al., *Chem. Abs.*, 78, 184, Abstract No. 78:107639c (1973).

T. A. Voronina et al., Ann. Ist. Super. Sanita, 24, N 3, pp. 461–466 (1988).

T. A. Voronina et al., *Ann. Ist. Super. Sanita*, 26, N 1, pp. 55–60 (1990).

T. A. Voronina et al., *Drug Development Research, 14, 353–358 (1988).*

BIOLOGICALLY ACTIVE N-ACYLPROLYDIPEPTIDES HAVING ANTIAMNESTIC, ANTIHYPOXIC AND ANOREXIGENIC EFFECTS

CROSS REFERENCE TO RELATED APPLICATIONS

The present application is a Continuation-In-Part application of U.S. application Ser. No. 07/868,000, filed Apr. 14, 1992, now abandoned.

BACKGROUND OF THE INVENTION

Nootropic agents (cognitive enhancers) constitute a promising group of medicines. Known nootropic agents include piracetam (N-carbamido-methyl-pyrrolidone-2), which was introduced into wide medical practice in the early 1980s. Other N-substituted-2-pyrrolidones (e.g. etiracetam, oxiracetam, aniracetam, pramiracetam, rolziracetam, etc.) have been synthesized.

U.S. Pat. No. 4,743,616 to Tanaka et al. describes N-acyl pyrrolidine compounds having endopeptidase inhibitory activity and which are reported to exhibit antiamnestic effects. Unlike the piracetam derivatives, the compounds described by Tanaka et al. contain a proline group.

Biologically active N-terminal pyroglutamic acid compounds having the formula:

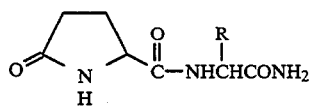

have been reported by T. Gudasheva and R. Ostrovskaya (*Chem. Pharmac. J.*, 1985, N 11, pp. 1322–1329). Another reported (T. A. Gudasheva et al., *Chem. Pharmac. J.*, 1988, N 3, pp. 271–275) biologically active compound is N-acylproline having the formula:

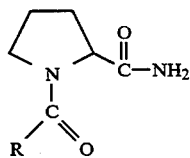

A substantial need exists for highly active and nontoxic nootropic agents which can be used for treatment of mental decline, caused by different damaging factors. The present invention is directed to addressing this need.

SUMMARY OF THE INVENTION

The present invention relates to a novel group of compounds, which possess different types of psychotropic activity, particularly antiamnestic, antihypoxic and anorexigenic effects. The invention also relates to a method for chemical synthesis of such novel compounds as well as their use as drugs for treatment, especially of different forms of memory disturbances.

The present invention provides N-acyl-prolyldipeptides of the formula:

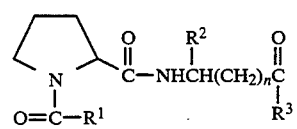

wherein:
$R^1 = (C_4-C_5)$ alkyl, cycloalkyl, aralkyl, or aryl;
$R^2 = H$, $(C_1-C_4)$ alkyl, carbamidoalkyl, or carbalkoxyalkyl;
$R^3 = NH_2$, NH(alkyl), N(alkyl)$_2$, OH, or alkoxy; and
$n = 0-3$, preferably 0–2.

In the compound represented by Formula 1, $R^1$ is preferably selected from the group consisting of isobutyl, pentyl, 1-adamantyl, phenyl, phenylmethyl, and phenylpropyl, and more preferably selected from the group consisting of phenylmethyl and phenyl. $R^3$ is preferably selected from the group consisting of amino ($NH_2$), methylamino ($NHCH_3$), dimethylamino ($N(CH_3)_2$), hydroxy (OH), and ethoxy ($OC_2H_5$), and more preferably selected from the group consisting of amino and ethoxy.

Compounds of Formula 1 differ from known nootropic agents in that the compounds of Formula 1 contain in their structure a residue of the natural amino acid, L-proline (instead of pyrrolidone), together with a residue of a second natural amino acid. These N-acyl-L-proline derived dipeptide compounds have an extremely low toxicity and are highly active.

Following are compounds illustrative of the scope of this invention:

I. N-phenacetyl-L-prolylglycine ethyl ester
II. N-phenacetyl-L-prolylglycine amide
III. N-phenacetyl-L-prolyl-β-alanine ethyl ester
IV. N-phenylacetyl-L-prolyl-β-alanine amide
V. N-phenylacetyl-L-prolyl-L-aspartic acid diethyl ester
VI. N-phenylacetyl-L-prolyl-L-asparagine amide
VII. N-benzoyl-L-prolylglycine ethyl ester
VIII. N-isovaleryl-L-prolylglycine ethyl ester
IX. N-phenylacetyl-L-prolyl-L-valine ethyl ester
X. N-benzoyl-L-prolyl-L-valine ethyl ester
XI. N-benzoyl-L-prolyl-β-alanine ethyl ester
XII. N-benzoyl-L-prolyl-β-alanine amide
XIII. N-benzoyl-L-prolylglycine amide
XIV. N-phenylacetyl-L-prolylglycine N-methylamide
XV. N-phenylacetyl-L-prolylglycine dimethylamide
XVI. N-phenylacetyl-L-prolyl-L-glutamic acid diethyl ester
XVII. N-phenylacetyl-L-prolyl-L-leucine amide
XVIII. N-phenylacetyl-L-prolylglycine
XIX. N-phenylacetyl-L-prolyl-GABA methylester
XX. N-phenylacetyl-L-prolyl-L-alanine ethyl ester
XXI. N-caproyl-L-prolylglycine ethyl ester
XXII. N-(1-adamantoyl)-L-prolylglycine ethyl ester
XXIII. N-phenylbutyl-L-prolyl-glycine ethylester The present invention is also directed to a pharmaceutical compositions and methods of medical treatment that include as an active substance a pharmaceutically effective amount of an N-acylprolyldipeptide of Formula 1, as defined above, preferably a compound of the formula:

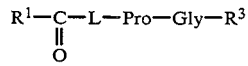

wherein R¹ is preferably selected from the group consisting of iso-butyl, pentyl, 1-adamantyl, phenyl, phenylmethyl, and phenylpropyl; and R³ is preferably selected from the group consisting of $NH_2$, $NHCH_3$, $N(CH_3)_2$, OH, and $OC_2H_5$. More preferably, the pharmaceutical compositions and methods of treatment of the present invention include an effective dose of a compound of the formula:

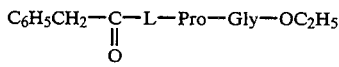

Herein, a "pharmaceutically effective amount" or "effective amount" is an amount capable of effectively treating the syndrome from which the patient suffers.

The compounds of the invention possess psychotropic activity, including antiamnestic activity, and improvement of cognitive function damaged by brain trauma, intoxication, aging, and hypoxia. These compounds also display anorexigenic effect, antialcoholic activity, and cause diminished mental decline in prenatally alcoholized offsprings.

The present invention is also directed to various methods of treating human suffering by administrating an effective dose of the compounds of the invention. Such methods include treating human suffering from mental decline caused by brain trauma, aging, senile dementia, and mentally retarded children; obesity; chemical toxicity CNS effects, preferably caused by lead poisoning; sickle cell anemia; benzodiazepine withdrawal syndrome, which is manifested by aggression, anxiety, and seizures; and alcohol withdrawal.

DETAILED DESCRIPTION OF THE INVENTION

Compounds according to Formula 1 above were obtained by the well-known methods of peptide synthesis. The ordinary process for producing the compounds under consideration consists of combining the required amino acids by condensation, as a rule, in the homogenous phase.

Condensation in the homogenous phase may be performed in the following way:
a) condensation of an amino acid having a free carboxyl group and another protected reactive group, with an amino acid having a free amino group and other protected reactive groups in the presence of a condensing agent, such as carbodiimide;
b) condensation of an amino acid having an activated carboxyl group and another protected reactive group, with an amino acid that has a free amino group and other protected reactive groups;
c) condensation of an amino acid having a free carboxyl group and another protected reactive group, with an amino acid having an activated amino group and other protected reactive groups.

Activation of the carboxyl group may be performed by converting it into a chloranhydride, azide, anhydride group or activated ester, such as N-oxysuccinimide, N-oxybenztriazole, penthachlorophenylicorparanitrophenylic ester. The amino group may be activated by converting it into a phosphite-amide or by resorting to the "phosphoraso" method.

The most common techniques for the above condensation reactions are: the carbodiimide method; the azide method; the method of mixed anhydrides; and the method of activated esters. These methods are described in "The Peptides", Vol. 1, 1965 (Academic Press), E. Schröder and K. Lübke, or in "The Peptides", Vol. 1, 1979 (Academic Press), E. Gross and L. Meinhofen.

The preferable condensation methods of obtaining Formula 1 peptides are the method of mixed anhydrides or the carbodiimide method. The condensation reaction performed by the method of mixed anhydrides is preferably conducted under "Andersonian" conditions [G. W. Anderson et al., J. Am. Chem. Soc., 89, 5012–5017 (1967)]. The carboxyl component (i.e., for the formation of a mixed anhydride of N-acylproline) is preferably activated by isobutyl chloroformate. Ethyl chloroformate and methyl chloroformate may also be used.

Preferred solvents are a mixture of ethyl acetate and dimethylformamide, pure dimethylformamide, and chloroform. Preferred tertiary bases are N-methylmorpholine, N-ethylmorpholine, and triethylamine.

The condensation reaction performed by the carbodiimide method is preferably conducted in the presence of oxybenzotriazole [W. Konig and R. Geiger, Chem. Ber., 103, 788–798 (1979)]. Condensation by the carbodiimide method may also be conducted in the presence of other additives, such as para-nitrophenol, pentachlorphenol, or N-oxysuccinimide.

The reactive groups that are not supposed to be involved in the condensation reaction can be protected by groups that can be easily removed through hydrolysis or reduction, for example. Thus, a carboxyl group may be protected by esterification with ethanol, methanol, tertiary butanol, benzyl alcohol. The groups that usually effectively protect an amino group are acid groups, for example: acid group from aliphatic, aromatic, heterocyclic carboxylic acid, such as acetyl, benzoyl, pyridine carboxyl; the acid group from carbonic acid, such as ethoxycarbonyl, benzyloxycarbonyl, tetra-butyloxycarbonyl group; or the acid group derived from sulfoacid, such as the para-toluenesulfonyl acid group.

Functional peptide derivatives of Formula 1 mean: (1) N-acyl derivatives from aliphatic or aromatic acids; (2) esters derived from low-alkyl alcohols; and (3) amides or monoalkyl- or dialkyl-substituted amides, in which the alkyl groups have one or two C-atoms.

During the synthesis of the claimed prolyl dipeptides, N-acyl derivatives were preferably obtained through the use of proline, preliminarily acylated by a suitable acyl group. This acyl group also functioned as a protective group in the course of further synthesis. It is also possible to insert the desired amine group after the peptide synthesis by acylating the dipeptide by routine methods. The preferred N-acyl groups are N-phenylacetyl and N-benzoyl.

Peptide esters according to Formula 1 are preferably obtained by the use of an amino acid in the form of the desired ester. They may also be obtained by suitable esterification of the obtained peptide. Preferably, the esters are derived from methanol or ethanol.

Amides of the peptides according to Formula 1 are obtained by ammonolysis (i.e., reaction with $NH_3$) of the alkyl ester of a corresponding dipeptide, or by using in the reaction an amino acid in the form of the desired amide. Amides of dipeptides may also be obtained by inserting an amide group into the corresponding dipeptide by some suitable method, for example, treatment with an amine in the presence of a condensing agent. The preferable amides are nonsubstituted amides, monomethyl-amides, and dimethyl-amides.

The compounds of the present invention were assessed for their ability to prevent memory impairment induced by maximal electroshock, or scopolamine administration. Unlike N-acylpyrrolidine compounds of the type described by Tanaka et al., supra, the compounds of the present invention are not believed to inhibit prolyl endopeptidase activity. As is described in the Examples, the tested compounds exhibit antiamnestic activity (Example 12). A preferred compound having Formula I (see Table 1) was demonstrated to be able to facilitate different phases of memory formation: acquisition of the information, retention and retrieval in various procedures of passive and active avoidance (Examples 12, 13). This compound was shown to be able to increase the degree of acute habituation (Example 14). The Compound I prevents mental decline, induced by frontal lobectomy (Example 15), prenatal alcoholization or prenatal hypoxia (Example 16) and aging (Example 17). This substance exhibited antihypoxic activity (Example 18).

While piracetam was observed to exert some of the above-described activities, the level of active dose for piracetam is 200–800 mg/kg. In contrast to this, substances in accordance with the present invention exert their effects in a dose between about 0.1–0.5 mg/kg.

Compound I described herein has an additional useful property: anorexigenic effect (Example 19). In contrast to known anorexigenic drugs, Compound I fails to evoke the adrenergic stimulation (excitation, increase of blood pressure, etc.). Compound I is also nontoxic (Example 20), and active when administered perorally (Example 12). Compound I was shown to be able to diminish the syndrome of benzodiazepine withdrawal diminishing the anxiety, aggressiveness and pentylentetrazole induced kindling (Example 21).

Substances according to the present invention can be used in any form which is suitable for oral administration, such as pills, tablets and dragee. The presently described substances can be administered parenterally, by injection or infusion in the form of pharmaceutical preparations composing the active ingredient in combination with a pharmaceutically accepted carrier. The substances of the present invention can be used for the treatment of human mental decline, induced by brain trauma, intoxications, age-related processes, Korsakoff syndrome, Alzheimers disease, organic brain syndrome, alcoholism including prenatal alcohol damage, hypoxia, mental retardation of children , obesity arteriosclerotic cerebrovascular disease, brain damage due to congenital malformations or genetic abnormalities, chemical toxicity CNS effects including lead poisoning, drug abuse treatment including withdrawal and abstinence maintenance, and certain hematologic disorders including sickle cell anemia. Preferably, the substances can be used in doses of 0.5–5.0 mg per day.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXAMPLES

The invention is further illustrated by the following specific examples.

The following abbreviations are used:

Pro-prolyl
Asp-aspartyl
Asn-asparaginyl
Val-valyl
Ala-alanyl
γ-Ala -γ-alanyl
Leu-leucyl
Gly-glycyl
Glu-glutamyl
EtOH-ethanol
MeOH-methanol
DMF-dimethylformamide
DCC-dicyclohexylcarbodimide
DCU-dicyclohexylurea
EtAC-ethyl acetate
BZ-benzoyl
Ad-1-adamantyl
OHBt-1-oxibenztriazole
$Et_3N$-triethylamine
Phac-phenylacetyl
TLC-thin layer chromatography In examples the following apparatus were used: melting points were determined on a sulfur acid apparatus in the open capillars and were not corrected. Specific optical rotations were recorded on automatic polarimeter Perkin-Elmer-241. Nuclear magnetic resonance spectra were obtained on AC-250 Bruker spectrometer. Chemical shifts are expressed ppm downfield from $Me_4Si$. For the resonance signals the following abbreviations are used: s-singlet, d-doublet, t-triplet, q-quartet, m-multiplet. Spin-spin coupling constants are given in Hz. Thin layer chromatography (TLC) was performed on Merk silica gel 60F254, plates and spots were developed in an iodine chamber or in UF light.

In vivo experiments employed randomly bred male albino rats of approximately 180–220 g and/or randomly bred male albino mice of about 18–22 g. In vivo alcohol tests employed offspring of alcoholized mothers of similar type. Wister strain male albino rats at 24–26 months were used in the experiments with aging.

EXAMPLE 1

Synthesis of Ethyl Ester of
N-phenylacetyl-L-prolyl-glycine
N-Phac-L-Pro-Gly-OEt (I)

a) N-Phenylacetyl-L-proline, N-Phac-L-Pro-OH

To 5.75 g (0.05 mole) L-proline in 25 ml 2N NaOH were added dropwise under stirring at a temperature below 10° C., 12.5 ml 4N NaOH and 6.6 ml (0.05 mole) N-phenylacetyl chloride (b.p. 89°–90° C./10 Torr). Reaction mixture was stirred 15 min, extracted by EtAc to remove chloride then it was acidified by 2N HCl to pH~3, extracted by chloroform, dried over sodium sulfate and evaporated. 6.2 g N-Phac-L-Pro-OH were obtained as white crystals, m.p. 150°–152° C., $[α]_D^{20}$—60.5° (c 0.4, DMF), $R_f$ 0.66 (Kiesel-gel, dioxane-water 9:1).

$^1$NMR-spectrum in CDCl$_3$ δ (ppm): 1.77–2.29 (m, $C^\beta H_2$—$C^\gamma H_2$ Pro, 4H); 3.40–3.63 (m, $C^\delta H_2$, Pro 2H); 3.63 and 3.73 (each s, C$\underline{H}_2$—$C_6H_5$, 2H); 4.56 and 4.38

(each dd, C$^\alpha$H Pro, 1H); 7.18–7.39 (m, CH$_2$C$_6$H$_5$, 5H); 11.38 (broad s, COOH, 1H). Analysis Calcd. for C$_{13}$15NO$_3$: C, 66.93; H, 6.49; N, 6.00. Found: C, 66.65; H, 6.40; N, 5.86.

b) Ethyl ester of N-phenylacetyl-L-prolyl-glycine.

To solution of 2.33 g (0.01 mole) N-Phac-L-Pro-OH (m.p. 150°–151° C.) in 50 ml DMF were added under stirring at −10° C., 1.39 ml (0.01 mole) Et$_3$N and then 1.34 ml (0.01 mole) isobutylchloroformiate. In 2 minutes to reaction mixture were added dropwise for 25 minutes, 1.4 g (0.01 mole) hydrochloride of glycine ethyl ester (m.p. 140°–142° C.) and solution 1.39 ml (0.01 mole) Et$_3$N in 25 ml DMF to avoid temperature rise. Then stirring was prolongated to 30 min. at cooling and 1.5 hours at room temperature. The precipitate was filtered and the filtrate evaporated in vacuo, the residue was dissolved in CHCl$_3$, solution was washed by 5% NaHCO$_3$, water, 1N HCl and again water, dried over sodium sulfate and evaporated. A resulting 1.66 g (54%) of oil was blended with ether into white crystals, m.p. 96°–97° C.; [α]$_D^{20}$ −120° C. (c 0.4, CHCl$_3$). R$_f$ 0.80 (Kiesel-gel, dioxane-water, 9:1). $^1$H-NMR spectrum in (CD$_3$)$_2$SO, δ (ppm): 1.18 (t, CH$_3$CH$_2$O, 55% 5H); 1.17 (t, CH$_3$CH$_2$O, 45% 3H); 1.65–2.35 (m, C$^\beta$H$_2$—C$^\gamma$H$_2$ Pro, 4H); 3.2–3.4 (m, C$^\delta$H$_2$, Pro, 2H); 3.40 (s, CH$_2$—C$_6$H$_5$, 45% H); 3.67 (s, CH$_2$—C$_6$H$_5$, 55% 2H); 3.80 (d, C$^\alpha$H$_2$ Gly, J=5.9, 55% 2H); 3.86 (d, J=5.9, C$^\alpha$H$_2$Gly, 45% 2H); 4.08 (q, CH$_3$—CH$_2$—O, 55% 2H); 4.09 (q, CH$_3$—CH$_2$—O, 45% 2H); 4.32 (dd, C$^\alpha$H, Pro, 55% 1H); 4.48 (dd, C$^\alpha$H, Pro, 45% 1H); 7.1–7.6 (m, CH$_2$C$_6$H$_5$, 5H); 8.29 (t, J=5.9, NH Gly, 55% 1H); 8.63 (t, J=5.9, NHGly, 45% 1H). Analysis Calcd. for C$_{17}$H$_{22}$N$_2$O$_4$: C, 64.15; H, 6.92; N, 8.80. Found: C, 63.93; H, 6.81, N, 9.07.

EXAMPLE 2

Synthesis of N-phenylacethyl-L-prolyl-glycin-amide Phac-L-Pro-Gly-NH$_2$ (II)

N-Phac-L-Pro-Gly-OEt (0.53 g, m.p. 96°–97° C., [α]$_D^{20}$ −122.0 in CHCl$_3$, see Example 1b) was dissolved in 25 ml of saturated NH$_3$ ethanol. The reaction mixture was maintained for 12–16 hours at room temperature. Ethanol was then evaporated and the residue was washed with ether. The yield of amide II was 0.5 g, which was obtained as an oil. R$_f$ 0.36 (Kiesel-gel, CHCl$_3$—MeOH, 9:1). [α]$_D^{20}$58.5 (c, 0.2, CHCl$_3$). $^1$H-NMR spectrum in CDCl$_3$, δ (ppm): 1.8–2.3 (m, C$^\beta$H$_2$—C$^\gamma$H$_2$, Pro, 4H); 3.3–3.5 (m, C$^\delta$H$_2$, Pro, 2H); 3.55–3.75 (m, AB part ABX system, C$^\alpha$H$_2$ Gly, 2H); 3.66 (s, CH$_2$—C$_6$H$_5$, 2H); 4.07 (dd, C$^\alpha$H, Pro, 1H); 4.37 (t, NHGly, 1H); 5.63 and 7.86 (every s, NH$_2$); 7.2–7.4 (m, C$_6$H$_5$, 5H). Analysis Calcd for C$_{15}$H$_{19}$N$_3$O$_3$: C, 62.53; H, 6.48; N, 14.61. Found: C, 62.28; H, 6.54; N, 14.53.

EXAMPLE 3

Synthesis of ethylester of N-phenyl-L-prolyl-β-alanine N-Phac-L-Pro-β-Ala-OEt (III)

To solution of 0.61 g (2.6 mmol) N-phenylacetyl-L-proline (m.p. 151° C., [α]$_D^{20}$ −60.5° in DMF) in 25 ml CHCl$_3$ at −10° C., 0.29 ml (2.6 mmol) N-methylmorpholine was added followed by 0.35 ml (2.6 mmol) isobutylchloroformate. At 2 minutes, 0.4 g (2.6 mmol) hydrochloride of β-alanine ethyl ester (m.p. 69°–71° C.) and 0.29 ml N-methylmorpholine in 4 ml CHCl$_3$ were added to the reaction mixture solution. Stirring was prolonged under cooling for 40 minutes and then 2 hours at room temperature. The residue was filtered and the solvent evaporated on a rotary evaporator. The remainder was dissolved in CHCl$_3$ and washed with 5% solution of NaHCO$_3$, water, 1N HCl, water, and then dried over sodium sulfate and evaporated. The yield was 0.58 g or (98%) N-Phac-L-Pro-β-Ala-OEt, which was obtained as a transparent oil. R$_f$ 0.52 (Kiesel-gel, CHCl$_3$—MeOH, 9:1); R$_f$ 0.53 (Kiesel-gel, dioxane-water, 9:1); [α]$_D^{20}$92.25 (c 0.3, CHCl$_3$).

$^1$H-NMR-spectrum in (CD$_3$)$_2$SO, δ (ppm): 1.17 (t, CH$_3$CH$_2$—O, 68% 3H); 1.13 (t, CH$_3$CH$_2$O, 32% 3H); 1.7–2.2 (m, C$^\beta$H$_2$—C$^\gamma$H$_2$, Pro, 4H); 2.42 (m, C$^\alpha$H$_2$β-Ala, 2H); 3.2–3.3 (m, C$^\delta$H$_2$, Pro, 2H); ~3.40 (s, CH$_2$C$_6$H$_5$, 32% 2H) under HDO-Signal; 3.66 (m, CH$_2$C$_6$H$_5$, 68% 2H); 4.01 (q, CH$_3$—CH$_2$O, 32% 2H); 4.04 (q, CH$_3$—CH$_2$O, 68% 2H); 4.41 (m, C$^\beta$H$_2$β-Ala, 2H); 4.21 (dd, C$^\alpha$H, Pro, 1H); 7.1–7.36 (m, CH$_2$—C$_6$H$_5$, 5H); 7.93 (t, NH, 1H). Analysis Calcd for C$_{18}$H$_{24}$N$_2$O$_4$: C, 65.03; H, 7.29; N, 8.42. Found: C, 65.37; H, 7.77; N, 8.38.

EXAMPLE 4

Synthesis of amide of N-phenylacethyl-L-prolyl-β-alanine N-Phac-L-Pro-β-Ala-NH$_2$ (IV)

Gaseous ammonia was bubbled to saturation through an ethanol solution (15 ml) of 0.36 g ethyl ester of N-phenylacetyl-L-prolyl-β-alanine, obtained as in Example 3. After standing overnight the solvent was evaporated and the residue was purified by column chromatography (silica gel), using CHCl$_3$ as eluent. The amide IV was obtained as an oil, yield 0.22 g (61%). R$_f$ 0.28 (Kiesel-gel, CHCl$_3$-methanol, 9:1); [α]$_D^{20}$ −22.8° (c 0.33; CHCl$_3$).

$^1$H-NMR (Me$_2$SO-d$_6$), δ (ppm): 1.69–2.2 (m, C$^\beta$H$_2$—C$^\gamma$H$_2$ Pro, 4H); 2.16–2.31 (m, C$^\alpha$H$_2$β-Ala, 2H); 3.1–3.3 (m, C$^\beta$H$_2$, β-Ala, 2H); 3.3–3.45 (m, C$^\delta$H$_2$, Pro, 2H); 3.66 (s, CH$_2$—C$_6$H$_5$, 2H); 4.22 and 4.41 (every dd, C$^\alpha$H Pro, 1H); 6.84, 7.36 and 6.86, 7.38 (each br. s, NH$_2$, 2H); 7.12–7.35 (m, CH$_2$C$_6$H$_5$, 5H); 7.89 and 8.22 (each t, NH β-Ala, 1H). Analysis Calcd. for C$_{16}$H$_{21}$N$_3$O$_3$: C, 63.34; H, 6.99; N, 13.85. Found: C, 63.81; H, 7.03; N, 14.01.

EXAMPLE 5

Synthesis of diethyl ester of N-phenylacetyl-L-prolyl-L-asparaginic acid, N-Phac-L-Pro-L-Asp (OEt)$_2$ (V)

To a well-stirred solution of N-phenylacetyl-L-proline (1 g; 4.3 mmol) in absolute EtAc (40 ml), N-methylmorpholine (0.48 ml; 4.3 mmol) was added at −10° C. Following this addition, iso-BuOC(O)Cl (0.57 ml; 4.3 mmol) was added, and after 2–3 minutes a mixture of L-Asp (OEt)$_2$.HCl (0.91 g; 4.3 mmol), N-methylmorpholine (0.48 ml; 4.3 mmol), and EtAc (15 ml) were added. Stirring was continued for 1 hour at −10° C. After the mixture was allowed to stand for 1 hour, the precipitate was separated by filtration, the solvent was evaporated, and the residue was dissolved in a mixture of ethanol and ether. The resulting precipitate was separated, mother liquor was evaporated, and the residue (1.65 g) was purified by column chromatography (Silica gel), using CHCl$_3$ and the mixture CHCl$_3$-EtOH, as eluents. The diethyl ester of N-phenylacetyl-L-prolyl-L-asparaginic acid was obtained as an oil; R$_f$ 0.87 (Kiesel-gel, CHCl$_3$-EtOH, 9:3) [α]$_D^{20}$ −38.0 (C 2.2; CHCl$_3$).

$^1$H-NMR (Me2SO-d6), δ (ppm): 1.23 (t, J=7.16 Hz, CH$_3$CH$_2$O, 90% 3H); 1.24 (t, J=7.16, CH$_3$CH$_2$O, 10% 3$\overline{\text{H}}$ ); 4.10 (q, CH$_3$CH$_2$—O, 90% $\overline{\text{2H}}$); 4.12 (q, CH$_3$CH$_2$—O, 10% 2H); $\overline{1.25}$ (t, J=7.14, CH$_3$CH$_2$O, 90% 3H ); 1.26 (t, J=7.14, CH$_3$CH$_2$O, 10% $\overline{\text{3H}}$ ); 4.19 (q, CH$_3$CH$_2$O, 90% 2H); 4.2$\overline{1}$ (q, CH$_3$CH$_2$O, 10% 2H); 1.75–2.40 (m, C$^β$H$_2$—C$^γ$H$_2$, Pro, 4$\overline{\text{H}}$); 3.45–3.65 (m, C$^δ$C$_2$ Pro, 2H ); 4.58 (dd, J=8.00; J=2.59; C$^α$H Pro, 1H); 2.78; 2.95 (dd, AB-part of ABX-system, J$_{AB}$=17.04; J$_{AX}$=4.88; J$_{BX}$=4.88; C$^β$H$_2$ Asp, 90% 2H); 2.80; 3.00 (dd, C$^β$H$_2$ Asp, 10% 2H); 4.81 (dt, J=C$^α$H NH 8.50; C$^α$H Asp 1H); 7.5 (d, J=8.50; NH Asp, 90% 1H) 7.03 (d, J=8.40; NHAsp, 10% 1H); 3.70 (s, CH$_2$C$_6$H$_5$, 2H); 7.20–7.36 (m, C$_6$H$_5$, 5H). Analysis Calcd. for C$_{21}$H$_{28}$N$_2$O$_6$: C, 62.35; H, 6.99; N, 6.92. Found: C, 62.63; H, 7.01; N, 6.74.

EXAMPLE 6

Synthesis of amide of N-phenylacetyl-L-prolyl-L-asparagine, N-Phac-L-Pro-L-Asn-NH$_2$ (VI)

Gaseous ammonia was bubbled to saturation through a methanol solution (25 ml) of 0.5 g N-Phac-L-Pro-L-Asp (OEt)$_2$, obtained as in Example 5, at 0° C. After standing overnight the solvent was evaporated, the residue was dissolved in the warm mixture of ethanol and chloroform, and pentane was added to precipitation. The resulting precipitate was collected and dried to obtain the amide of N-phenylacetyl-L-prolyl-L-asparagine (0.45 g): m.p. 170°–172° C., R$_f$0.24 (Kiesel-gel, CHCl$_3$-EtOH, 9:3), [α]$_D^{20}$ −55.7° (C 1.4; DMSO).

$^1$H-NMR [(Me2SO-d6)] (ppm): 1.60–2.30 (m, C$^β$H$_2$—C$^γ$H$_2$ Pro, 4H); 2.35–2.50 (m, C$^β$H$_2$ Asn, 2H) under signal of solvent; 3.63 (s, $\underline{\text{CH}}_2$—C$_6$H$_5$, 2H ); 4.36 (m, C$^α$H Pro, 1H ); 4.4–4.6 (m, C$\overline{^α\text{H}}$ Asn, 1H); 6.80–7.60 (m, C$_6$H$_5$, 5H); 6.8–7.1 (s, NH$_2$, 4H); 8.15; 8.25; 8.35 (each d, NH Asn, 1H). Analysis Calcd. for C$_{17}$H$_{22}$N$_4$O$_4$: C, 58.94; H, 6.41; N, 16.16. Found: C, 59.23; H, 6.66; N, 16.04.

EXAMPLE 7

Synthesis of ethyl ester of N-benzoyl-L-prolylglycine, N-BZ-L-Pro-Gly-OEt (VII)

a) N-benzoyl-L-proline

To a well-stirred solution of L-proline (5.75 g, 0.05 mmole) in 2N aq. NaOH (25 ml), 4N NaOH (12.5 ml) and benzoyl chloride (5.8 ml, 0.05 mole) were added dropwise from different drop funnels, maintaining the temperature near 0°–4° C. The mixture after 15 minutes was acidified with 1N HCl. The resulting oil was extracted with CHCl$_3$, the combined organic extract was dried (MgSO$_4$), and the solvent was removed. Ether was added to the residue and the mixture was allowed to stand overnight at 0° C. The crystals of N-benzoyl-L-proline were separated. Yield 3.42 g (60%), m.p. 152°–154° C., [α]$_D^{20}$ −68.5° (c 0.4; CHCl$_3$); R$_f$0.13 (Kiesel-gel, CHCl$_3$—CH$_3$OH, 9:1). Analysis Calcd. for C$_{12}$H$_{13}$NO$_3$: C, 65.73; H, 5.99; N, 6.39. Found: C, 65.64; H, 6.03; N, 6.54.

b) Ethyl ester of N-benzoyl-L-prolylglycine

To a well stirred solution of N-benzoyl-L-proline (2.19 g, 0.01 mole) in the mixture of absolute EtAc (50 ml) and DMF (10 ml), N-methylmorpholine (1.12 ml; 0.01 mole) and iso-BuOC(O)Cl (1.34 ml; 0.01 mole) were added dropwise at −10° C. After 2 minutes a mixture of NH$_2$CH$_2$COOEt.HCl (1.4 g; 0.01 mole), N-methylmorpholine (1.12 ml; 0.01 mole), and DMF (20 ml) was added. After stirring for 30 minutes under cooling and for 1.5 hours at room temperature the solvent was removed in vacuo. The residue was dissolved in chloroform, washed with 5% aq. NaHCO$_3$, 1N aq. HCl, H$_2$O and then dried with Na$_2$SO$_4$. After filtration the solvent was evaporated. To the residue ether was added, and the resulting crystals of ester VII were separated. Yield 1.67 g (76%), m.p. 63°–65° C., [α]$_D^{20}$148.0° (c 0.4; CHCl$_3$); R$_f$0.71 (Kiesel-gel, CHCl$_3$—CH$_3$OH, 9:1).

$^1$H-NMR (Me2SO-d6) (ppm): 1.18 (t, J=7.04, CH$_3$CH$_2$O, 75% 3H); 1.09 (t, J=7.04, CH$_3$CH$_2$O, 25% $\overline{\text{3H}}$); 1.73–2.28 (m, C$^β$H$_2$—C$^γ$H$_2$ Pro, $\overline{\text{4H}}$); 3.3–3.4 (m, C$^γ$H$_2$ Pro, 2H); 3.60 and 3.74 (dd, J=5.87 and J=8.22 C$^α$H$_2$ Gly, 25% 2H); 3.85 (d, J=5.87, C$^α$H$_2$Gly, 75% 2H); 4.10 (q, CH$_3$$\underline{\text{CH}}_2$O), 75% 2H); 4.13 (q, CH$_3$$\underline{\text{CH}}_2$O, 25% 2H ); 4.47 (d$\overline{\text{d}}$, C$^α$H Pro, 25% 1H); 4.48 (dd, $\overline{\text{C}^α\text{H}}$ Pro, 75% 1H); 7.33–7.62 (m, C$_6$H$_5$ 5H); 8.36 (t, J=5.87; NH, 75% 1H); 8.40 (t, J=5.87; NH, 25% 1H). Analysis Calcd. for C$_{16}$H$_{20}$N$_2$O$_4$: C, 63.14; H, 6.61; N, 9.20. Found: C, 63.56; H, 6.87; N, 9.48.

EXAMPLE 8

Synthesis of ethyl ester of N-iso-valeryl-L-prolylglycine, iso-C$_4$H$_9$C(O)-Pro-Gly-OEt (VIII)

a) N-iso-valeryl-L-proline

To a well stirred solution of L-proline (1.15 g; 0.01 mole) in 2N aq. NaOH (5 ml), 4N aq. NaOH (2.5 ml) and iso-valeryl chloride (1.4 ml; 0.012 mole) were added simultaneously dropwise maintaining the temperature near 0°–4° C. After 15 minutes, the mixture was acidified (pH 2–3) with 1N HCl and extracted with CHCL$_3$. The combined organic extract was dried using MgSO$_4$, and the solvent was removed. N-iso-valeryl-L-proline was obtained as an oil. Yield 0.85 g, R$_f$=0.66 (Silica gel, n-C$_4$H$_9$OH-AcOH-H$_2$O, 5:1:2); [α]$_D^{20}$ −129.3° (c 0.6; CHCl$_3$).

$^1$H-NMR CDCl$_3$, δ (ppm): 0.99 (d, —CH($\underline{\text{CH}}_3$)$_2$, 6H); 2.25 (m, $\underline{\text{CH}}$(CH$_3$)$_2$, 1H); 2.3 (m, $\underline{\text{CH}}_2$CH($\overline{\text{CH}}_3$)$_2$, 2H); 1.9–2.65 (m, C$^α$H$_2$—C$^γ$H$_2$, 4H); 3.45–3.70 (m, C$^δ$H$_2$Pro, 2H); 8.85 (br. s, COO$\underline{\text{H}}$, 1H). Analysis Calcd. for C$_{10}$H$_{17}$NO$_3$: C, 60.27; $\overline{\text{H}}$, 8.62; N, 7.02. Found: C, 60.34; H, 8.74; N, 7.23.

b) Ethyl ester of N-iso-Valeryl-L-prolylglycine

To a well stirred solution of N-iso-valeryl-L-proline (0.74 g; 0.0037 mole) in abs. EtAc (15 ml), N-ethylmorpholine (0.47 ml; 0.0037 mole) and iso-BuOC(O)Cl (0.5 ml; 0.0037 mole ) were added. After 2–3 minutes, a mixture of NH$_2$CH$_2$COOEt.HCl (0.52 g; 0.0037 mole), N-ethylmorpholine (0.47 ml; 0.0037 mole), and DMF (10 ml) was added dropwise, while maintaining the temperature at −10° C. to −5° C. Stirring was continued for 30 minutes under cooling and 1.5 hours at room temperature. The precipitate was separated by filtration, and the mother liquor was evaporated. The residue was dissolved in chloroform, washed with 5% aq. NaHCO$_3$, H$_2$O, 1N aq. HCl, H$_2$O and then dried with MgSO$_4$. After filtration the solvent was evaporated and the residue (0.6 g) was purified by column chromatography (Silica gel), using CHCl$_3$ as eluent. Yield VIII as viscous colorless liquid was 0.49 g (49%); R$_f$0.55 (Silica gel, CHCl$_3$—CH$_3$OH, 9:1), [α]$_D^{20}$ −113.4° (c 0 3; CHCl$_3$).

$^1$H-NMR (CDCl$_3$), δ (ppm): 0.99 (d, J=5.97, CH($\underline{\text{CH}}_3$)$_2$, 6H); 2.22 (m, $\underline{\text{CH}}$Me$_2$, 1H); 1.27 (t, J=7.16; OCH$_2$$\underline{\text{CH}}_3$, 3H); 4.18 (q, O$\underline{\text{CH}}_2$CH$_3$, 2H); 1.75–2.60 (m, $C^\beta H_2$—$C^\gamma H_2$ Pro, 4H); 3.35–3.70 (m, $C^\delta H_2$Pro, 2H); 3.96 and 4.02 (each dd, $C^\alpha H_2$ Gly, 2H); 3.85–4.10 (m, CH$_2$CHMe, 2H); 6.50 and 7.59 (each t, NHGly, 1H). Analysis Calcd. for $C_{14}H_{24}N_2O_4$: C, 59.12; H, 8.52; N, 9.85%. Found: C, 58.78; H, 8.74; N, 9.87.

EXAMPLE 9

Synthesis of N-benzoyl-L-prolyl-β-alanine ethyl ester, N-BZ-L-Pro-β-Ala-OEt (XI)

To a DMF solution (25 ml) of 0.9 g (6 mmol) β-Ala-OEt.HCl, 1.3 g (6 mmol) N-BZ-L-Pro-OH, and 0.87 g (6.4 mmol) N-hydroxy-benztriazole, 0.83 ml (6.01 mmol) of triethylamine were added. The mixture was cooled to 3° C. and 1.54 g (7.5 mmol) of DCC were added. The mixture was allowed to stand at 3° C. overnight, at room temperature for 1.5 hours, and then it was cooled to −15° C. The resulting DCU was removed by filtration. Aqueous potassium bicarbonate was added to the filtrate to obtain precipitation. The precipitate was filtered, washed with water and recrystallized from a mixture of ethanol and water. The solid was filtered, washed and dried. Obtained 1.5 g (78.9%) of product, m.p. 88°–89° C., $[\alpha]_D^{20}$ −114.0° (c 0.5; CHCl$_3$), R$_f$ 0.86 (Kiesel-gel, CHCl$_3$—C$_2$H$_5$OH 9:1).

$^1$H-NMR spectrum in DMSO-d6, δ (ppm): 1.03 and 1.07 (each t, CH$_3$—CH$_2$O, 3H); 1.6–2.3 (m, $C^\beta H_2$—$C^\gamma H_2$Pro, 4H); 2.45 (t, $C^\alpha H_2$ β-Ala, 2H); 4.04 (q, CH$_3$CH$_2$O, 2H); 3.14 and 3.40 (each m, $C^\beta H_2$ Ala, 2H); 3.3–3.6 (m, $C^\gamma H_2$ Pro, 2H); 4.37 and 4.14 (each dd, $C^\alpha H$ Pro, 1H); 7.33–7.62 (m, C$_6$H$_5$, 5H); 8.02 and 8.00 (each t, NH, 1H). Analysis Calcd. for $C_{17}H_{22}N_2O_4$: C, 64.15; H, 6.92; N, 8.80. Found: C, 64.23; H, 7.03; N, 8.91.

EXAMPLE 10

Synthesis of N-phenylacetyl-L-prolylglycinmethylamide, N-Phac-L-Pro-Gly-NHMe (XIV)

A solution of 1.6 g (5 mmol) of N-Phac-L-Pro-Gly-OEt in 50 ml of ethanol was cooled to 0° C., then monomethylamine (dried through NaOH trap) was bubbled through the solution for 30 minutes. The solution was maintained at room temperature for 5 hours. Ethanol was evaporated in vacuo. Ether was added to the residue and the solid filtered, dried in vacuo at 25° C. to obtain 1.6 g (99%) of the product, m.p. 185°–186.5° C. $[\alpha]_D^{20}$ −36.0° (c 0.5; CHCl$_3$), R$_f$ 0.66 (Kiesel-gel, dioxane-water 9:1).

$^1$H-NMR spectrum in DMSO-d6, δ (ppm): 1.66–2.24 (m, $C^\beta H_2$—$C^\gamma H_2$ Pro, 4H); 2.49 (d, NHCH$_3$, 85% 3H); 2.60 (d, NHCH$_3$, 15% 3H); 3.61 and 3.63 (each m, $C^\alpha H_2$Gly, 85% 2H); 3.52 and 3.62 (each m, $C^\alpha H_2$ Gly, 15% 2H); 3.40–3.60 (m, $C^\alpha H_2$Pro, 2H); 3.70 (s, CH$_2$Ar, 85% 2H); 3.68 (s, CH$_2$Ar, 15% 2H); 4.23 (dd, $C^\alpha H$ Pro, 85% 1H); 4.44 (dd, $C^\alpha H$ Pro, 15% 1H); 7.16–7.36 (m, C$_6$H$_5$, 5H); 7.58 (q, NH—CH$_3$, 85% 1H); 7.84 (q, NHCH$_3$, 15% 1H); 8.38 (t, NHGly, 85% 1H); 8.36 (t, NHGly, 15% 1H). Analysis Calcd. for $C_{16}H_{21}N_3O_3$: C, 63.34; H, 6.93; N, 13.86. Found: C, 63.61; H, 6.75; N, 14.01.

EXAMPLE 11

Synthesis of N-phenylacetyl-L-prolylglycine, N-Phac-L-Pro-Gly-OH (XVIII)

A suspension of 1.06 g (3.5mmol) of N-phenylacetyl-L-prolylglycine, ethyl ester (Example 1) in 5 ml of 1N NaOH was stirred at room temperature for 3 hours to obtain solution. Then it was acidified by 2N HCl to pH 3. The solution was evaporated in vacuo to obtain an oil. The oil was dissolved in 15 ml chloroform, the unsolubilized part was removed by filtration, and the filtrate was evaporated. Ether was added to the residue and the solid was filtered, and dried in vacuo at room temperature to obtain 0.9 g (89.9%) of the product, m.p. 159°–160° C. (subl.), R$_f$ 0.54 (Kiesel-gel, dioxane-water 9:1), $[\alpha]_D^{20}$ −85.8° (c 0.5 CHCl$_3$).

$^1$H-NMR spectrum in DMSO-d6, δ (ppm): 1.80–2.25 (m, $C^\beta H_2$—$C^\gamma H_2$ Pro, 4H); 3.36–3.63 (m, $C^\delta H_2$Pro, 2H); 3.64 and 3.68 (each s, CH$_2$—C$_6$H$_5$, 2H); 3.86; 4.00 and 3.83; 4.02 (each dd, $C^\alpha H_2$Gly, 2H); 4.57 and 4.44 (each dd, $C^\alpha H$ Pro, 1H); 7.11–7.38 (m, C$_6$H$_5$, 5H); 7.52 and 7.32 (each t, NH, 1H); 12.06 (br. s, COOH, 1H). Analysis Calcd. for $C_{15}H_{18}N_2O_4$: C, 62.04; H, 6.22; N, 9.64. Found: C, 62.11; H, 6.26; N, 10.09.

FURTHER PREPARATIONS

In the same manner as in Example 1, a dipeptide of formula N-Phac-L-Pro-L-Val-OEt (IX) was obtained using as starting reactants N-Phac-L-Pro-OH and Val-OEt.HCl. This product had the following properties. Yield 72%, oil, R$_f$ 0.64 (Kiesel-gel, dioxane-water 9:1), $[\alpha]_D^{20}$ −99.3° (c 0.35; CHCl$_3$).

$^1$H-NMR spectrum in CDCl$_3$, δ (ppm): 0.83 and 0.86 (each d, J=6.9 Hz, $C^\beta H(CH_3)_2$Val, 90% 6H); 0.89 and 0.95 (each d, J=6.9 Hz, $C^\beta H(CH_3)_2$Val, 10% 6H); 1.27 (t, CH$_3$CH$_2$O, 90% 3H); 1.28 (t, CH$_3$CH$_2$O, 10% 3H); 1.7–2.5 (m, $C^\beta H_2$—$C^\gamma H_2$ Pro, 4H); 2.25 (m, $C^\beta H$ Val, 1H); 3.4–3.7 (m, $C^\delta H_2$Pro, 2H); 3.7 (s, CH$_2$Ar, 2H); 4.18 (q, CH$_3$CH$_2$O, 2H); 4.38 (dd, $C^\alpha H$ Val, J=8.4 Hz, J=4.9 Hz, 90% 1H); 4.54 (dd, $C^\alpha H$ Val, 10% 1H); 4.68 (dd, $C^\alpha H$ Pro, 1H); 7.28 (m, C$_6$H$_5$, 5H); 7.44 (d, J=8.4 Hz, NH, 90% 1H); 6.48 (d, NH, 10% 1H). Analysis Calcd. for $C_{20}H_{28}N_2O_4$: C, 66.63; H, 7.84; N, 7.76. Found: C, 66.58; H, 7.74, N, 7.85.

In the same manner as in Example 2, a dipeptide of formula: N-BZ-L-Pro-β-Ala-NH$_2$ (XII) was obtained using as starting reactants N-BZ-L-Pro-β-Ala-OEt. This product had the following properties: yield 75%, m.p. 135°–137° C. (ether); R$_f$ 0.21 (Kiesel-gel, CHCl$_3$—C$_2$H$_5$OH, 9:1); $[\alpha]_D^{20}$ −41.6° C. (c 0.45 CHCl$_3$).

$^1$H-NMR spectrum in DMSO-d6, δ (ppm): 1.68–2.20 (m, $C^\beta H_2$—$C^\gamma H_2$ Pro, 4H); 2.24 (t, $C^\alpha H_2$β-Ala, 2H); 3.21 and 3.10 (each dt, $C^\beta H_2$—β-Ala, 2H); 3.30–3.68 (m, $C^\delta H_2$Pro, 2H); 4.39 and 4.11 (each dd, $C^\alpha H$ Pro, 1H); 6.86–7.22 (m, C$_6$H$_5$ and NH$_2$, 7H); 7.98 and 7.87 (each t, NH, 1H). Analysis Calcd. for $C_{15}H_{19}N_3O_3$: C, 62.28; H, 6.57; N, 14.53. Found: C, 62.31; H, 6.70; N, 14.58.

In the same manner as in Example 4, a dipeptide of formula N-BZ-L-Pro-Gly-NH$_2$ (XIII) was obtained from N-BZ-L-Pro-Gly-OEt. Yield 76%, m.p. 64°–74° C. (amorphous), R$_f$ 0.54 (Kiesel-gel, CHCl$_3$—C$_2$H$_5$OH 3:1); R$_f$ 0.3 (Kiesel-gel, CHCl$_3$—C$_2$H$_5$OH 9:1), $[\alpha]_D^{20}$ −47.9° (c 0.45 CHCl$_3$).

$^1$H-NMR spectrum in DMSO-d6, δ (ppm): 1.68–2.00 and 2.05–2.30 (m, $C^\beta H_2$—$C^\gamma H_2$ Pro, 4H); 3.3–3.45 (m, $C^\delta H_2$ under HDO, 2H); 3.53–3.75 (m, $C^\alpha H_2$Gly, 2H); 4.20 and 4.40 (each m, $C^\alpha H$ Pro, 1H); 6.95–7.65 (m, C$_6$H$_5$ and NH$_2$, 7H); 8.05 and 8.41 (each t, NH, 1H). Analysis Calcd. for $C_{14}H_{17}N_3H_3$: C, 61.09; H, 6.20; N, 15.27. Found: C, 61.32; H, 6.31; N, 15.21.

The following were prepared in a manner corresponding to Example 1:

Dipeptide of formula N-Phac-L-Pro-Gly-NMe$_2$ (XV), yield 78%, the oil, R$_f$=0.68 (Kiesel-gel, dioxan-water 9:1), $[\alpha]_d^{20} = -147.1°$, (C=0.1, CHCl$_3$); $^1$H NMR spectrum in DMSO-d$_6$, δ (ppm): 1.71-2.06 (m, C$^\beta$H$_2$—C$^\gamma$H$_2$ Pro, 4H); 2.83, 2.93 and 2.84, 2.96 (each s, N(CH$_3$)$_2$, 6H); 3.3-3.6 (m, C$^\delta$H$_2$ Pro 2H); 3.67 (s, CH$_2$—C$_6$H$_5$, 2H); 3.89 and 3.95 (each d, C$^\alpha$H$_2$ Gly, 2H); 4.37 and 4.52 (dd each, C$^\alpha$H Pro 1H); 7.15-7.34 (m, C$_6$H$_5$, 5H); 7.88 and 8.24 (each t, NH, 1H). Analysis Calcd. for C$_{17}$H$_{23}$N$_3$O$_3$: C, 64.32; H, 7.32; N, 13.23. Found: C, 64.53; H, 7.48; N, 13.01.

Dipeptide of formula N-Phac-L-Pro-L-Glu-(OEt)$_2$ (XVI), yield 69%; the oil, R$_f$=0.9 (Kiesel-gel, dioxan:-water 9:1), R$_f$=0.7 (Kiesel-gel, CHCl$_3$:EtOH 3:1) $[\alpha]_D^{20} = -45.9°$, (c=0.3, CHCl$_3$); $^1$H NMR spectrum in CDCl$_3$, δ (ppm): 1.25 and 1.27 (each t, 2 CH$_3$—CH$_2$—O, 6H); 1.76-2.49 (m, C$^\beta$H$_2$—C$^\gamma$H$_2$ Pro, C$^\beta$H$_2$—C$^\gamma$H$_2$ Glu, 8H); 3.39-3.92 (m, C$^\delta$H$_2$ Pro, 2H); 3.71 (s, CH$_2$—C$_6$H$_5$, 2H); 4.13 and 4.19 (each q, 2 CH$_3$—CH$_2$—O, 4H); 4.35 and 4.49 (each m, C$^\alpha$H Glu, 1H); 4.49 and 4.61 (each dd, C$^\alpha$H Pro, 1H); 7.15-7.38 (m, C$_6$H$_5$, 5H); 7.30 and 7.43 (each d, NH Glu, 1H). Analysis Calcd. for C$_{22}$H$_{30}$N$_2$O$_6$: C, 63.13; H, 7.24; N, 6.69. Found: C, 63.24; H, 7.11; N, 6.81.

Dipeptide of formula N-Phac-L-Pro-L-Leu-NH$_2$ (XVII), yield 83%, m.p. 174°-175° C., R$_f$=0.5 (Kiesel-gel, CHCl$_3$:EtOH 9:1) $[\alpha]_D^{20} = -101.4°$, (C=0.4, CHCl$_3$); $^1$H NMR spectrum in DMSO-d$_6$, (ppm): δ0.82 and 0.88 (each d, C$^\beta$H(CH$_3$)$_2$ Leu, 6H); 1.50 (m, C$^\beta$H Leu, 1H); 1.31-1.93 and 1.7-2.40 (each m, C$^\beta$H$_2$—C$^\gamma$H$_2$ Pro, 4H); 3.43-3.67 (m, C$^\delta$H$_2$ Pro, 2H); 3.69 (s, CH$_2$—C$_6$H$_5$, 2H); 4.17 and 4.34 (each m, C$^\alpha$H Leu, 1H); 4.28 and 4.58 (each dd, C$^\alpha$H Pro, 1H); 7.0 and 7.13 (each s, NH$_2$); 7.15-7.35 (m, C$_6$H$_5$, 5H); 7.10-7.45 (m, two s, C$_6$H$_5$ and NH$_2$); 7.86 and 8.27 (each d, NH Leu, 1H). Analysis Calcd. for C$_{19}$H$_{27}$N$_3$O$_3$*0.5-H$_2$O: C, 64.37; H, 7.98; N, 11.85. Found: C, 64.13; H, 7.70; N, 11.95.

Dipeptide of formula N-Phac-L-Pro-GABA-OMe (XIX), yield 86%, the oil, R$_f$=0.65 (Kiesel-gel, CHCl$_3$:EtOH 9:1) $[\alpha]_D^{20} = -93.6°$, (C=0.4, CHCl$_3$); $^1$H NMR spectrum in DMSO-d$_6$, δ (ppm): 1.63 (m, C$^\beta$H$_2$ GABA, 2H); 1.65-2.15 (m, C$^\beta$H$_2$—C$^\gamma$H$_2$ Pro, 4H); 2.29 (m, C$^\alpha$H$_2$ GABA 2H); 3.05 (m, C$^\gamma$H$_2$ GABA 2H); 3.2-3.4 (m, C$^\delta$H$_2$ Pro under HDO, 2H); 3.58 (s, OCH$_3$, 3H); 3.66 (s, CH$_2$—C$_6$H$_5$, 2H); 4.20 and 4.40 (each dd, C$^\alpha$H Pro, 1H); 7.02-7.37 (m, C$_6$H$_5$, 5H); 7.85 and 8.20 (each t, NH, 1H). Analysis Calcd. for C$_{18}$H$_{24}$N$_2$O$_4$: C, 65.03; H, 7.29; N, 8.42. Found: C, 65.37; H, 7.41; N, 8.28.

Dipeptide of formula N-Phac-L-Pro-L-Ala-OEt (XX), yield 78%, m.p. 48°-51° C., R$_f$=0.75 (Kiesel-gel, dioxan:water 10:1), $[\alpha]_D^{20} = -99.2°$, (C=0.6, CHCl$_3$); $^1$H NMR spectrum in DMSO-d$_6$, δ (ppm): 1.16 (t, CH$_3$—CH$_2$—O, 3H); 1.27 and 1.31 (d each, CH$_3$ Ala, 3H), 1.68-2.27 (m, C$^\beta$H$_2$—C$^\gamma$H$_2$ Pro, 4H); 3.46-3.61 (m, C$^\delta$H$_2$ Pro, 2H); 3.65 (s, CH$_2$—C$_6$H$_5$, 2H); 3.98-4.14 (q, CH$_3$—CH$_2$—O, 2H); 4.19 and 4.29 (each dq, C$^\alpha$H Ala 1H); 4.34 and 4.48 (each dd, C$^\alpha$H Pro, 1H); 7.12-7.36 (m, C$_6$H$_5$, 5H); 8.28 and 8.60 (each d, NH Ala, 1H). Analysis Calcd. for C$_{18}$H$_{24}$N$_2$O$_4$: C, 65.03; H, 7.29; N, 8.42. Found: C, 65.07; H, 7.32; N, 8.45.

Dipeptide of formula N-C$_5$H$_{11}$C(O)-L-Pro-Gly-OEt (XXI), yield 54%, the oil, R$_f$=0.81 (Kiesel-gel, dioxan:-water 9:1), R$_f$=0.86 (Kiesel-gel, CHCl$_3$:EtOH 9:1) $[\alpha]_D^{20} = -216°$, (C=0.2, CHCl$_3$); $^1$H NMR spectrum in DMSO-d$_6$, δ (ppm): 0.90 and 0.91 (each t, CH$_3$—(CH$_2$)$_4$—, 3H); 1.19 (t, CH$_3$—CH—O, 3H); 1.27, 1.50 and 2.25 (two m and t, CH$_3$—(CH$_2$)$_4$, 8H); 1.70-2.20 (m, C$^\beta$H$_2$—C$^\gamma$H$_2$ Pro, 4H); 3.35 3.50 (m, C$^\delta$H$_2$ Pro, 2H); 3.78 and 3.82 (each d, C$^\alpha$H$_2$, Gly, 2H); 4.08 (1, CH$_3$—CH$_2$—O, 2H); 4.30 and 4.36 (each dd, C$^\alpha$H Pro, 1H); 8.15 and 8.36 (each t, NH Gly, 1H). Analysis Calcd. for C$_{15}$H$_{26}$N$_2$O$_4$: C, 60.39; H, 8.78; N, 9.38. Found: C, 60.35; H, 8.84; N, 9.31.

Dipeptide of formula N-AdC(O)-L-Pro-Gly-OEt (XXII), yield 81%, m.p. 177°-179° C., R$_f$=0.93 (Kiesel-gel, CHCl$_3$:EtOH 2:3) $[\alpha]_D^{20} = -66.2°$, (C=0.6, CHCl$_3$); $^1$H NMR spectrum in DMSO-d$_6$, δ (ppm): 1.18 (t, CH$_3$—CH$_3$—O, 3H); 1.66, 1.88 and 1.96 (m, Ad); 1.6-2.0 (m, C$^\beta$H$_2$—C$^\gamma$H$_2$ Pro under Ad); 3.23-3.37 (m, C$^\delta$H Pro, 2H); 3.72 and 3.84 (each dd, C$^\alpha$H$_2$, Gly J=16.5, 2H); 4.08 (q, CH$_3$—CH$_2$—O, 2H); 4.39 (m broad, C$^\alpha$H Pro 1H); 8.07 (t broad, NH Gly, 1H). Analysis Calcd. for C$_{20}$H$_{30}$N$_2$O$_4$: C, 66.28; H, 8.33; N, 7.73. Found: C, 66.49; H, 8.36; N, 8.13.

Dipeptide of Formula N-C$_6$H$_5$(CH$_2$)$_3$C(O)-L-Pro-Gly-OEt (XXIII), yield 84%, the oil, R$_f$=0.87 (Kiesel-gel, dioxan:water 9:1), R$_f$=0.75 (Kiesel-gel, CHCl$_3$:EtOH 9:1) $[\alpha]_D^{20} = -90.1°$, (C=0.8, CHCl$_3$); $^1$H NMR spectrum in DMSO-d$_6$, δ (ppm): 1.18 (t, CH$_3$—CH$_2$—O, 3H); 1.64-2.23 (m, C$^\beta$H$_2$—C$^\delta$H$_2$ Pro, 4H); 1.79, 2.28, and 2.59 (m, two t, —(CH$_2$)$_3$—, 6H); 3.2-3.6 (m, C$^\delta$H$_2$ Pro, 2H); 3.78 and 3.81 (each d, C$^\alpha$H$_2$, Gly 2H); 4.07 and 4.09 (each q, CH$_3$—CH$_2$—O, 2H); 4.33 and 4.36 (each dd, C$^\alpha$H Pro, 1H); 7.04-7.35 (m, C$_6$H$_5$, 5H); 8.18 and 8.47 (each t, NH Gly, 1H). Analysis Calcd. for C$_{19}$H$_{26}$N$_2$O$_3$: C, 69.05; H, 7.95; N, 8.47. Found: C, 69.21; H, 7.99; N, 8.52.

EXAMPLE 12

Compounds according to the present invention, including the compounds described in Examples 1-11, were checked for their ability to prevent memory decline evoked by maximal electroshock (MES) or scopolamine in the passive avoidance step-through paradigm (equipment of Laffaette Co., USA). The experiments described herein (Examples 12, 13, 15, and 19) were carried out using randomly bred male albino rats of a weight of approximately 180-220 g. Each substance was administered in dose 0.1 mg/kg intraperitoneally 15 min. before passive avoidance training. Amnesia was produced by transcorneal maximal electroshock immediately after learning or scopolamine (1 mg/kg, subcutaneously) administration 30 min. before learning. The retention was tested 24 hours later by the measurement of latency of the entering of the dark compartment.

The degree of antiamnestic activity was estimated according to Buttler's modified formula:

$$\frac{\text{Latency drug} - \text{Latency amnesia}}{\text{Latency control} - \text{latency amnesia}} \times 100\%$$

The higher the magnitude of this indicator the more is the antiamnestic activity.

In control groups of animals MES as well as scopolamine caused amnesia: latency of the entering of the dark compartment was significantly decreased.

The compounds of the present invention caused a pronounced antiamnestic effect: increasing values of latency and of AA index (Tables 1, 2).

TABLE 1

Antiamnestic activity of drugs (dose of 0.1 mg/kg) checked in passive avoidance paradigm with maximal electroshock

| No. | Substance R$^1$ | R$^2$ | R$^3$ | Latency (sec.) n | Control | Amnesia | Amnesia + subst. | AA % |
|---|---|---|---|---|---|---|---|---|
| I. | CH$_2$C$_6$H$_5$ | H | OC$_2$H$_5$ | 0 | 45 | 14 | 25 | 36** |
| II. | CH$_2$C$_6$H$_5$ | H | NH$_2$ | 0 | 153 | 19 | 56 | 27* |
| III. | CH$_2$C$_6$H$_5$ | H | OC$_2$H$_5$ | 1 | 131 | 25 | 56 | 29* |
| IV. | CH$_2$C$_6$H$_5$ | H | NH$_2$ | 1 | 98 | 26 | 64 | 52* |
| V. | CH$_2$C$_6$H$_5$ | CH$_2$COOC$_2$H$_5$ | OC$_2$H$_5$ | 0 | 173 | 41 | 80 | 29.5* |
| VI. | CH$_2$C$_6$H$_5$ | CH$_2$CONH$_2$ | NH$_2$ | 0 | 133 | 28 | 55 | 26* |
| VII. | C$_6$H$_5$ | H | OC$_2$H$_5$ | 0 | 95 | 3 | 37 | 37* |
| VIII. | iso-C$_4$H$_9$ | H | OC$_2$H$_5$ | 0 | 138 | 78 | 95 | 28* |
| IX. | CH$_2$C$_6$H$_5$ | CH(CH$_3$)$_2$ | OC$_2$H$_5$ | 0 | 133 | 39.6 | 39.7 | 0.0001 |
| X. | C$_6$H$_5$ | CH(CH$_3$)$_2$ | OC$_2$H$_5$ | 0 | 133 | 39.6 | 75.4 | 38 |
| XI. | C$_6$H$_5$ | H | OC$_2$H$_5$ | 1 | 102.7 | 51.6 | 62.8 | 21.9 |
| XII. | C$_6$H$_5$ | H | NH$_2$ | 1 | 102.7 | 51.6 | 59.4 | 15.2 |
| XIII. | C$_6$H$_5$ | H | NH$_2$ | 0 | 102.7 | 51.6 | 42.6 | −17.6 |
| XIV. | CH$_2$C$_6$H$_5$ | H | NHCH$_3$ | 0 | 102.7 | 51.6 | 47.7 | −7.6 |
| XV. | CH$_2$C$_6$H$_5$ | H | N(CH$_3$)$_2$ | 0 | 111.0 | 19 | 41.0 | 23.0 |
| XVI. | CH$_2$C$_6$H$_5$ | (CH$_2$)$_2$COOC$_2$H$_5$ | OC$_2$H$_5$ | 0 | 111.0 | 19 | 72.8 | 58.3* |
| XVII. | CH$_2$C$_6$H$_5$ | CH$_2$CH(CH$_3$)$_2$ | NH$_2$ | 0 | 138.9 | 60 | 66.3 | 7.9 |
| XVIII. | CH$_2$C$_6$H$_5$ | H | OH | 0 | 102.7 | 51.6 | 56.6 | 9.8 |
| XIX. | CH$_2$C$_6$H$_5$ | H | OCH$_3$ | 2 | 138.9 | 60 | 95.8 | 45.4* |
| XX. | CH$_2$C$_6$H$_5$ | CH$_3$ | OC$_2$H$_5$ | 0 | 138.9 | 60 | 68.6 | 10.8 |
| XXI. | (CH$_2$)$_4$CH$_3$ | H | OC$_2$H$_5$ | 0 | 133.9 | 60 | 76.1 | 20.2* |
| XII. | C$_{10}$H$_{15}$(Ad) | H | OC$_2$H$_5$ | 0 | 111.0 | 19 | 31.6 | 13.1* |
| XXIII. | (CH$_2$)$_3$CH$_5$ | H | OC$_2$H$_5$ | 0 | 111.0 | 19 | 31.0 | 12.6 |
| Piracetam, 200 mg/kg | | | | | 126.8 | 12 | 47.7 | 30.5* |

AA - antiamnestic activity estimated according to the Butler's modified formula.
*P < 0.05; **P < 0.01 in comparison with control.

TABLE 2

Influence of substances* on the amnestic effect of scopolamine (1 mg/kg subcutaneously 30 min. before the trial) in passive avoidance test.

| Substances | Latency (sec.) 0.9% Saline | Scopolamine | Scopolamine + substance | Aa** |
|---|---|---|---|---|
| I | 86.6 | 36 | 64.1 | 55.5 |
| II | 161.4 | 55.2 | 45.6 | −9.0 |
| III | 163.9 | 52.1 | 78.6 | 23.7 |
| IV | 138.9 | 47.1 | 94.9 | 52.1 |
| V | 158.9 | 58.3 | 48.1 | −10 |
| VI | 148 | 50.5 | 46.3 | −4.3 |
| Piracetam (200 mg/kg) | 118 | 28.9 | 64.2 | 39.3 |

*Substances were administered in the dose of 0.1 mg/kg 15 min. before the learning
**Aa is calculated according to the formula:
$$\frac{\text{Latency subst.} - \text{Latency Scopolamine}}{\text{Latency saline} - \text{Latency Scopolamine}} \times 100\%$$

Taking into consideration excellent antiamnestic activity of Compound I in both kinds of amnesia, this compound was chosen for further study.

It was shown that effectiveness of this substance is preserved after its peroral administration; converted U-shape dose-response relationship was demonstrated in the experiments with maximal electroshock amnesia (Table 3).

TABLE 3

Dose-response relationship for Compound I revealed in passive avoidance test with MES amnesia.

| Dose (mg/kg) per os compound I) | 0.1 | 0.3 | 0.4 | 0.5 | 0.7 | 0.9 | 1.0 | 1.2 | 1.5 |
|---|---|---|---|---|---|---|---|---|---|
| Antiamnestic activity (Aa) | 19* | 19** | 23* | 43* | 52* | 36* | 10* | 16 | 10 |

P < 0.05; **P < 0.01 in comparison with control animals.
Aa - antiamnestic activity in %.

The positive amnestic effect of Compound I was revealed also in the situation of undertraining of the passive avoidance reflex. The facilitating effect of compound I was shown in the case of its administration 15 min. before trial, immediately after it or 15 min. before the retrieval test (Table 4).

TABLE 4

Comparative activity of Compound I and piracetam in passive avoidance with different regimes of administration.

| Substance (mg/kg) | Mnestic activity (Ma, %%)^ | | |
|---|---|---|---|
| | Administration 15 min. before trial | Administration immediately after trial | Administration 15 min. before retrieval |
| Compound I 0.5, i.p. | 23* | 14.0* | 32* |
| Piracetam 200, i.p. | 20.0* | 1.0 | −15** |

*P < 0.05;
**P < 0.01 in comparison with control animals.
^Ma was calculated according to the formula:
$$\frac{\text{Latency drug} - \text{Latency control}}{180 \text{ seconds} - \text{Latency control}} \times 100\%$$

Compound I may facilitate all main phases of memory formation: input of information, consolidation and retrieval. Piracetam did not facilitate the retrieval in these experiments.

EXAMPLE 13

The influence of Compound I on the active avoidance learning was studied in shuttle-box test (Ugo Basile, Italy). The conditioned reflex of active avoidance had been developed for 5 days with 50 daily trials for each rat. The learning task consisted in the rats' avoiding of the electric shock applied through the cage floor directly after sound. Rats could avoid the shock by moving into another compartment of the cage, but only while the sound was present (3 sec.). Compound I (0.1 mg/kg daily i.p.), administered 14 days before the learning and every day during the learning, was demonstrated to be able to facilitate the learning ability (Table 5).

TABLE 5

The influence of Compound I on the learning ability estimated in shuttle-box test.

| Group | Percentage of the rats reached the stable avoidance | | | | |
|---|---|---|---|---|---|
| Days of learning | 1 | 2 | 3 | 4 | 5 |
| Control | 0 | 0 | 0 | 29 | 71 |
| Substance I | 0 | 15 | 43* | 57* | 67 |

*P < 0.05 in comparison to control.

In other experiments, stable active avoidance reaction was damaged by simultaneously switching of sound and electrical footshock for 5 trials. Compound I prevented the impairment of avoidance (Table 6).

TABLE 6

The influence of Compound I on the conditional active avoidance reflex after damage.

| Group | Before damage | Percentage of avoidances during 5 trials | | |
|---|---|---|---|---|
| | | 1-5th trials | After damage 6-10th trials | 11-15th trials |
| Control | 85.0 ± 6.3 | 60.0 ± 11.3* | 82.5 ± 10.3 | 85.0 ± 7.3 |
| Compound I | 88.9 ± 4.8 | 86.7 ± 3.3** | 88.9 ± 4.8 | 97.8 ± 2.2 |

*P < 0.01 in comparison with the amount of the avoidances before damage
**P < 0.01 in comparison with control

EXAMPLE 14

The effect of Compound I on acute habituation of locomotor activity was estimated according to diminution of locomotions during 30 minutes. Experiments were performed on outbred albino male mice (18–22 g) placed in groups of 10 animals in registration cage (Optovarimex, Colomb., USA).

Compound I, administered 15 minutes before the beginning of registration in the dose range 0.05–5.0 mg/kg was demonstrated to increase the degree of habituation ("negative learning") without changing of initial locomotor activity (Table 7).

TABLE 7

Effect of Compound I on habituation (extinction of exploratory behavior reaction)

| Dose, mg/kg | Habituation index^ | | | | |
|---|---|---|---|---|---|
| | 0.05 | 0.1 | 0.5 | 2.5 | 5.0 |
| Compound I | 30* | 10* | 15** | 25* | 27* |
| Control (saline) | 55 | 53 | 67 | 89 | 63 |

^ Habituation index - ratio of motor activity during last 5 minutes of recording to motor activity in the first 5 minutes of recording, in %%.
*P < 0.05
**P < 0.01

EXAMPLE 15

The impairment of learning and memory was achieved also by frontal lobectomy, which was performed after passive avoidance or active avoidance learning. Compound I (0.1 mg/kg) was administered beginning from the first post-operational day and lasting for 9 days. The testing was performed at 4th and 9th days. In the control group (false operation) the passive and active avoidance learning did not change. The frontal lobectomy has as a consequence the decrease of the latency of the entering of the dark compartment; Compound I restored the passive avoidance reaction (Table 8).

Lobectomized rats showed the whole absence of the active avoidance reflex at the 4th day and weak tendency to its restoration at 9th day. Compound I increased the percentage of the animals performing the active avoidance reaction and the coefficient of the preserving (Table 8).

TABLE 8

The influence of Compound I on mnestic functions in the lobectomized rats

| | FRONTAL LOBECTOMY | | | | |
|---|---|---|---|---|---|
| | | 4th day | | 9th day | |
| Groups | False Operation | Control | Comp I | Control | Comp. I |
| Passive avoidance test (latency, sec) | 180 | | | 51.9 | 141.2* |
| Active avoidance test - coeff. of preserving, %%** | 71.8 | 0 | 28.1* | 9 | 38.1* |
| %% of avoiding rats | 100 | 0 | 42.8* | 16.6 | 57.1* |

*P < 0.05 compared with control;
**this coefficient was calculated according to the formula:

$$\text{Coeff} = \frac{N_1 - N_4}{N_1} \times 100\% \text{ or } \frac{N_1 - N_9}{N_1} \times 100\%$$

where "N" means the amount of the trials, sufficient for the stable reflex before the operation ($N_1$), 4th ($N_4$), and 9th ($N_9$) days, respectively.

EXAMPLE 16

The cognitive impairment in the rat's offspring was provoked by prenatal alcoholization or prenatal hypoxia. Prenatal alcoholization was achieved by peroral administration of 5 g/kg/day (25% solution) ethanol to pregnant female rats during whole pregnancy. To achieve prenatal hypoxia the rats on the 15th day of pregnancy were placed into hypobaric barometric chamber (the "elevating" up 8500 m altitude; exposition for 2 hours).

The treatment of the offspring was performed from 8th day to 20th day. Compound I was administered in the dose of 0.1 mg/kg/day subcutaneously. The testing was performed on two-month old rats.

It has been established that both kinds of damage (alcoholization, hypoxia) caused learning disorders in active avoidance test. Early postnatal administration of Compound I restored learning activity (Table 9).

TABLE 9

Influence of Compound I on rat's offspring learning, damaged by prenatal alcoholization or prenatal hypoxia

| | Rats with reflex of active avoidance in %% | | | | | | |
|---|---|---|---|---|---|---|---|
| | Days of learning | | | | | Days of retention | |
| Group | 1 | 2 | 3 | 4 | 5 | 1 | 2 |
| Control | 0 | 9 | 50 | 73 | 86 | 68 | 79 |
| Prenatal alcoholization | 0 | 0 | 33 | 50^ | | 25^ | 65 |
| Prenatal alcoholization + Compound I | 0 | 0 | 55 | 82* | | 78* | 89 |
| Prenatal hypoxia | 0 | 0 | 0 | 31^ | 54^ | | |
| Prenatal + hypoxia | 0 | 0 | 25* | 68* | 88** | | |

TABLE 9-continued

Influence of Compound I on rat's offspring learning, damaged by prenatal alcoholization or prenatal hypoxia

| | Rats with reflex of active avoidance in %% | | | | | | |
|---|---|---|---|---|---|---|---|
| | Days of learning | | | | | Days of retention | |
| Group | 1 | 2 | 3 | 4 | 5 | 1 | 2 |
| Compound I | | | | | | | |

*$P < 0.05$
**$P < 0.01$ in comparison with damaged group
^ $P < 0.05$ in comparison with control Prenatal alcoholization was shown to diminish the degree of the habituation in the open field. Chronic postnatal administration of Compound I restored the normal course of the habituation (Table 10).

TABLE 10

Influence of compound I on locomotor activity of offspring after prenatal alcoholization

| | Number of horizontal movements | | |
|---|---|---|---|
| | Days of observation | | Coefficient of |
| Groups | 1 | 5 | Habituation |
| Control | 7.6 | 3.1 | 0.4 |
| Prenatal alcoholization | 10.0 | 8.1^ | 0.81^ |
| Prenatal alcoholization + Compound I | 8.2 | 3.7* | 0.45* |

*$P < 0.05$ in comparison with alcoholized group
^ $P < 0.05$ in comparison with control

EXAMPLE 17

The influence of Compound I on age-related mental decline was studied in experiments on 24-month Wistar rats. The substance was administered chronically in the dose of 0.1 mg/kg/day during 24 days, intraperitoneally before the testing and 14 days during testing.

Registration of the locomotor activity in the Optovarimex multichannel analyzer has shown that Compound I increased the initial horizontal activity being administered chronically. The testing of the activity during 5 minutes revealed the decrease of the motility, due to acute habituation ("negative learning"). This test is suitable for the study of nootropics. In the control group the coefficient of the habituation was 0.29. Compound I pretreated animals showed more pronounced habituation with coefficient 0.03 (Table 11).

TABLE 11

The influence of Compound I on the age-related mental decline

| | Locomotor activity (counts) | | | | |
|---|---|---|---|---|---|
| | Time of registration | | Coefficient of habituation (ratio - | Passive avoidance test (latency, sec) | |
| Groups | 1st min. | 5th min. | 5th min/1st min) | 24 hours | 14 days |
| Control | 244 | 72 | 0.29 | 111 | 107 |
| Compound I | 422* | 13* | 0.03* | 128 | 132* |

*$P < 0.05$ as compared to the control.

Chronic administration of Compound I facilitated the retention tested 24 hours and especially 14 days after learning in passive avoidance test (Table 11). It is evident from these experiments that Compound I is able to improve amnestic function in the old rats.

EXAMPLE 18

The protective effect of Compound I in hypoxia was assessed using the barometric chamber by "elevating" of the outbred albino mice (18–22 g) to the altitude of 11,000 m at a speed of 1000 m/min. After 1 hour exposition the percentage of surviving mice after 0.9% saline pretreatment was 15%. Compound I (0.5 mg/kg) 15 minutes before hypoxia increased this value to 43.7%.

EXAMPLE 19

The influence of Compound I on body weight and food consumption was studied in the experiments on the outbred rats. The substance, administered during 3 weeks in dose of 0.1 mg/kg/day intraperitoneally slowed the dynamics of weight increase in comparison to control: the increase of the weight (in %% to the initial one) was 12% in the treated group and 24% in the control group.

The amount of the consumed chow checked between 19th and 21st days was less for treated animals (39.5 g/day/rat) than for control ones (68.6 g/day/rat). The obtained data shows an anorexigenic effect of compound I.

EXAMPLE 20

Compound I was checked for gross behavior and acute toxicity in outbred male mice (18–22 g). Compound I in the dose range 1–10 mg/kg i.p. neither stimulated nor depressed the spontaneous motor activity and did not enhance the stimulating effect of amphetamine on it. In this dose range Compound I also did not change rectal temperature. In the dose of 25 mg/kg compound I diminished the stimulating effect of amphetamine.

Up to the dose of 500 mg/kg it did not change motor coordination (rota rod test) and did not disturb the general condition (gross behavior) of the animals.

In the dose of 500–3000 mg/kg i.p. it did not cause lethality at 24 hours. In the dose of 1000 mg/kg compound I caused excitement in 50% of animals. In the dose of 5000 mg/kg i.p. compound I caused death in 50% of animals.

EXAMPLE 21

The influence of Compound I on withdrawal syndrome caused by the interruption of chronic administration of benzodiazepine tranquilizer phenazepam (T. A. Voronina et al., In *Fenazepam*; A. V. Bogatsky, Ed.; Naukova dumka Publishers: Kiev, 1982; pp. 67–169) was studied in experiments on male albino rats weighing 190–200 g at the beginning and 300–350 g at the end of the experiment.

Phenazepam (2 mg/kg intraperitoneally) or saline (control group of rats) were given once daily for 57 days. The withdrawal syndrome occurred 24–72 hours after the last injection. The withdrawal syndrome in rats consisted in "anxiogenic-like" state aggressiveness and accelerated development of kindled seizures caused by pentylentetrazol. Compound I was administered to the withdrawn rats in doses of 0.5 mg/kg intraperitoneally 15 minutes prior to testing.

The conflict situation test was used to reveal the "anxiety" of rats (J. R. Vogel et al., *Psychopharmacologia*, 21, 1–7 (1971)). This experiment involved previous training of water deprivated rats to drink water from a trough. Next day electrical stimulation was given by a 0.5 mA electric current through the trough. A conflict situation was created by clashing of the two different reflexes (drinking and self-defense).

Rats withdrawn from phenazepam 24 hours after stopping a chronic exposure showed a reduction in the incidence of drinking compared with the control group. This behavior in the conflict situation test can be considered as "anxiogenic-like" one. Compound I antagonized the "anxiogenic-like" response to benzodiazepine withdrawal and increased incidence of drinking in the conflict situation (Table 12).

TABLE 12

The Effect of Compound I on the "Anxiogenic-Like" State Evoked by Phenazepam Withdrawal

| Groups | The amount of the Punishment Response |
| --- | --- |
| Control | 31.75 ± 6.44 |
| Phenazepam withdrawal + Saline | 12.08 ± 1.83* |
| Phenazepam withdrawal + Compound I | 48.40 ± 12.39** |

*P < 0.05 in comparison with the control group (Student t-test)
**P < 0.05 in comparison with the phenazepam withdrawal.

The threshold of the aggressive behavior was determined in the experiment on the rats (R. Tedeshi et al., *J. Pharmacol. Exp. Ther.*, 125, 28–34 (1959)). The paired rats were placed on the electrified floor; the strength of the current, which provokes the fighting, was registered.

Phenazepam withdrawn rats showed the decrease of this threshold. Compound I, being administered to the 24 hours withdrawn rats, was demonstrated to be able to increase the threshold of aggressive response (Table 13).

TABLE 13

The Effect of Compound I on the Aggressiveness Evoked by Phenazepam Withdrawal

| Groups | Aggression Threshold (mA) |
| --- | --- |
| Control | 0.71 ± 0.02 |
| Phenazepam# | 2.16 ± 0.2 |
| Phenazepam withdrawal + Saline## | 0.48 ± 0.03 |
| Phenazepam withdrawal + Compound## | 0.92 ± 0.1* |

*P < 0.05 in comparison with phenazepam withdrawal group (U - criterium).
Immediately after the last administration of phenazepam.
24 hours after the last administration of phenazepam.

The seizure reactions of rats were studied using chemical kindling (C.R. Mason et al., *Epilepsia*, 13, 663–674 (1972); R. M. Post et al., *Handbook of Biological Psychiatry*, Part IV, No. 7, Marcel-Dekker (1981) pp. 609–651) produced by small doses of pentylene-tetrazol (35 mg/kg, intraperitoneally) administered 24, 48 and 72 h after phenazepam withdrawal. The degree of seizures was evaluated by 4 points: tremor (1 point); jerk (2 point); clonic seizures (3 points); tonic seizures and death (4 points).

Our experiments pointed out that the pentylenetetrazol seizures were more pronounced in phenazepam withdrawn rats than in the control one. Compound I diminished the degree of kindling provoked by pentylenetetrazol (Table 14).

TABLE 14

The Effect of Compound I on Seizures Produced by Pentylenetetrazol (Kindling Test) During Phenazepam Withdrawal, 24, 48 and 72 hours after the Last Chronic Injection

| Groups | Seizure Reactions in Points (M ± m) | | |
| --- | --- | --- | --- |
| | 24 h | 48 h | 72 h |
| Control | 0.75 ± 0.32 | 1.0 ± 0.35 | 1.37 ± 0.33 |
| Phenazepam withdrawal + Saline | 1.0 ± 0.41 | 1.86 ± 0.25 | 2.37 ± 0.45 |
| Phenazepam withdrawal + Compound I | 0.25 ± 0.12 | 0.87 ± 0.1* | 0.5 ± 0.24* |

*P < 0.01 in comparison with 48 h phenazepam withdrawal group (u-test).

It is obvious from these experiments that Compound I is able to diminish the syndrome of benzodiazepines withdrawal: it decreases the anxiety, aggressiveness and pentylenetetrazol induced kindling.

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

We claim:

1. A compound of the formula:

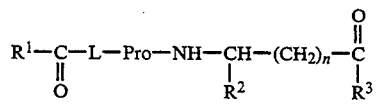

wherein:
(a) $R^1$ is $CH_2C_6H_5$;
(b) $R^2$ is selected from the group consisting of H, $CH_3$, $CH(CH_3)_2$, $CH_2CH(CH_3)_2$, $CH_2C(O)OC_2H_5$, $(CH_2)_2C(O)OC_2H_5$, and $CH_2C(O)NH_2$;
(c) $R^3$ is selected from the group consisting of OH, $OCH_3$, $OC_2H_5$, $NH_2$, $NHCH_3$, and $N(CH_3)_2$; and
(d) n=0–3.

2. The compound of claim 1 wherein $R^2$=H and n=0, said compound having the formula:

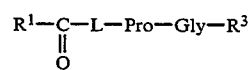

wherein $R^3$ is selected from the group consisting of OH, $OC_2H_5$, $NH_2$, $NHCH_3$, and $N(CH_3)_2$.

3. The compound of claim 2 wherein $R^1=CH_2C_6H_5$ and $R^3=OC_2H_5$.

4. The compound of claim 1 wherein $R^2$=H and n=1, said compound having the formula:

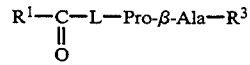

wherein:
(a) $R^1$ is $CH_2C_6H_5$ and
(b) $R^3$ is selected from the group consisting of $NH_2$ and $OC_2H_5$.

5. The compound of claim 1 wherein $R^2=CH(CH_3)_2$ and n=0, said compound having the formula:

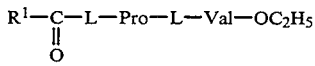

wherein $R^1$ is $CH_2C_6H_5$.

6. The compound of claim 1 wherein $R^1=CH_2C_6H_5$, $R^2=CH_2C(O)NH_2$, $R^3=NH_2$, and n=0, said compound having the formula:

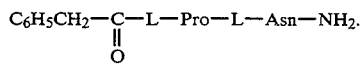

7. The compound of claim 1 wherein $R^1=CH_2C_6H_5$, $R^2=CH_2C(O)OC_2H_5$, $R^3=OC_2H_5$, and n=0, said compound having the formula:

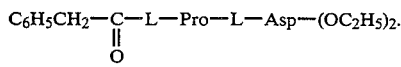

8. The compound of claim 1 wherein $R^1=CH_2C_6H_5$, $R^2=CH_2CH_2C(O)OC_2H_5$, $R^3=OC_2H_5$, and n=0, said compound having the formula:

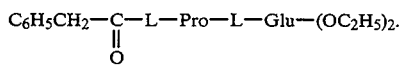

9. The compound of claim 1 wherein $R^1=CH_2C_6H_5$, $R^2=CH_2CH(CH_3)_2$, $R^3=NH_2$, and n=0, said compound having the formula:

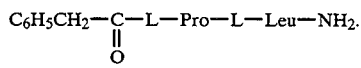

10. The compound of claim 1 wherein $R^1=CH_2C_6H_5$, $R^2=CH_3$, $R^3=OC_2H_5$, and n=0, said compound having the formula:

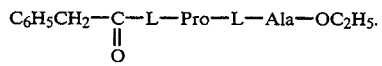

11. The compound of claim 1 wherein $R^1=CH_2C_6H_5$, $R^2=H$, $R^3=OCH_3$, and n=2, said compound having the formula:

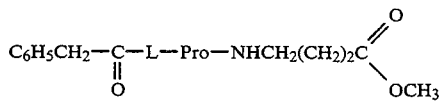

12. A pharmaceutical composition containing as an active substance a pharmaceutically effective amount of an N-acylprolyldipeptide having the formula:

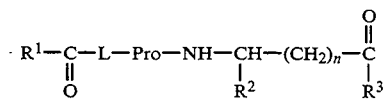

wherein:
(a) $R^1$ is $CH_2C_6H_5$;
(b) $R^2$ is selected from the group consisting of H, $CH_3$, $CH(CH_3)_2$, $CH_2CH(CH_3)_2$, $CH_2C(O)OC_2H_5$, $(CH_2)_2C(O)OC_2H_5$, and $CH_2C(O)NH_2$;
(c) $R^3$ is selected from the group consisting of OH, $OCH_3$, $OC_2H_5$, $NH_2$, $NHCH_3$, and $N(CH_3)_2$; and
(d) n=0-3.

13. The pharmaceutical composition of claim 12 wherein $R^2=H$ and n=0, said composition having the formula:

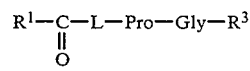

wherein $R^3$ is selected from the group consisting of $OC_2H_5$ and $NH_2$.

14. The pharmaceutical composition of claim 13 wherein $R^1=CH_2C_6H_5$ and $R^3=OC_2H_5$.

15. A method of treating obesity, said method comprising administrating an effective dose of a compound of the formula:

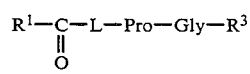

wherein:
(a) $R^1$ is $CH_2C_6H_5$; and
(b) $R^3$ is selected from the group consisting of $OC_2H_5$ and $NH_2$.

16. The method of claim 15 wherein the compound is of the formula $C_6H_5CH_2$—C(O)-L-Pro-Gly-$OC_2H_5$.

17. A method of treating sickle cell anemia, said method comprising administering an effective dose of a compound of the formula:

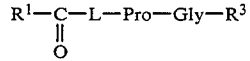

wherein:
(a) $R^1$ is $CH_2C_6H_5$; and
(b) $R^3$ is selected from the group consisting of $OC_2H_5$ and $NH_2$.

18. The method of claim 17 wherein the compound is of the formula $C_6H_5CH_2$—C(O)-L-Pro-Gly-$OC_2H_5$.

19. A method of diminishing mental decline in prenatally alcoholized offsprings, said method comprising administering an effective dose of a compound of the formula:

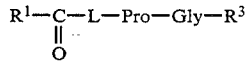

wherein:
(a) $R^1$ is $CH_2C_6H_5$; and
(b) $R^3$ is selected from the group consisting of $OC_2H_5$ and $NH_2$.

20. A method of diminishing benzodiazepine withdrawal syndrome, said method comprising administering an effective dose of a compound of the formula:

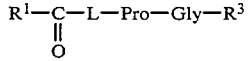

wherein:

(a) $R^1$ is $CH_2C_6H_5$; and (b) $R^3$ is selected from the group consisting of $OC_2H_5$ and $NH_2$.

21. A method of treating alcohol withdrawal, said method comprising administering an effective dose of a compound of the formula:

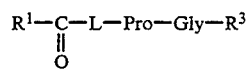

wherein (a) $R^1$ is $CH_2C_6H_5$; and (b) $R^3$ is selected from the group consisting of $OC_2H_5$ and $NH_2$.

22. A method of improving CNS functions, said method comprising administering an effective dose of a compound of the formula:

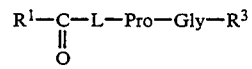

wherein (a) $R^1$ is $CH_2C_6H_5$; and (b) $R^3$ is selected from the group consisting of $OC_2H_5$ and $NH_2$.

23. A method of treating chemical dependency and toxicity, said method comprising administering an effective dose of a compound of the formula:

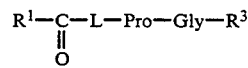

wherein:

(a) $R^1$ is $CH_2C_6H_5$; and (b) $R^3$ is selected from the group consisting of $OC_2H_5$ and $NH_2$.

24. The method of claim 23 wherein the compound is of the formula $C_6H_5CH_2$—C(O)-L-Pro-Gly-$OC_2H_5$.

25. The method of claim 23 wherein said chemical toxicity CNS effects are caused by lead poisoning.

* * * * *